(12) United States Patent
Habeger et al.

(10) Patent No.: US 10,271,852 B2
(45) Date of Patent: Apr. 30, 2019

(54) SPRING FOR MOVEABLE JAWS OF DEVICE AND DELIVERY SYSTEM FOR RELEASING THERAPEUTIC APPLIANCE

(71) Applicant: NDI Tip Teknolojileri Anonim Sirketi, Istanbul (TR)

(72) Inventors: Cam E. Habeger, Big Lake, MN (US); Michael J. Kuske, Waverly, MN (US); Civan Islak, Istanbul (TR); Sadik Semih Demiralp, Istanbul (TR); Garth W. Boyd, Ellington, CT (US)

( * ) Notice: Subject to any disclaimer, the term of this patent is extended or adjusted under 35 U.S.C. 154(b) by 315 days.

(21) Appl. No.: 14/944,209

(22) Filed: Nov. 17, 2015

(65) Prior Publication Data

US 2016/0066920 A1 Mar. 10, 2016

Related U.S. Application Data

(63) Continuation-in-part of application No. 14/277,022, filed on May 13, 2014.
(Continued)

(51) Int. Cl.
*A61B 17/00* (2006.01)
*A61B 17/12* (2006.01)

(52) U.S. Cl.
CPC .. *A61B 17/12145* (2013.01); *A61B 17/12113* (2013.01); *A61B 17/12031* (2013.01);
(Continued)

(58) Field of Classification Search
CPC .. A61B 2017/1205; A61B 2017/12054; A61B 2017/12059; A61B 2017/12063; A61B 2017/12068; A61B 2017/12072; A61B 2017/12077; A61B 2017/12081; A61B 2017/12086; A61B 2017/1209; A61B 2017/12095; A61B 2017/00867; A61B 2017/303; A61B 2017/305; A61B 2017/2926; A61B 2017/2927; A61B 2017/2929; A61B 2017/293; A61B 2017/2931; A61B 2017/2938; A61B 17/12022; A61B 17/12031; A61B 17/12109; A61B 17/12113; A61B 17/12118; A61B 17/29; A61B 17/282; A61B 2017/2932; A61B 2017/2933;
(Continued)

(56) References Cited

U.S. PATENT DOCUMENTS 5,989,242 A * 11/1999 Saadat ............. A61B 17/12022
606/1
6,277,125 B1 * 8/2001 Barry ............... A61B 17/12022
606/108
(Continued)

*Primary Examiner* — Darwin P Erezo
*Assistant Examiner* — Katherine H Schwiker
(74) *Attorney, Agent, or Firm* — Damian Wasserbauer, Esq.; Wasserbauer Law LLC

(57) ABSTRACT

The present invention relates to a spring to return more quickly the jaws of a gripper assembly of a delivery system for deploying an embolic coil. Each of the jaws and spring are formed of shape memory alloy configured to be movable between a first position and a second position and returning to the first position, with the spring tension increasing the speed of the return to the first position of the jaws of the gripper assembly. The gripper assembly may be used to insert, retract, reconnect, and rapidly disconnect from the embolic coil.

7 Claims, 5 Drawing Sheets

Related U.S. Application Data

(60) Provisional application No. 62/238,694, filed on Oct. 7, 2015.

(52) U.S. Cl.
CPC ........... *A61B 2017/00867* (2013.01); *A61B 2017/12054* (2013.01); *A61B 2017/12077* (2013.01)

(58) Field of Classification Search
CPC ..... A61B 2017/2934; A61B 2017/2937; A61F 2/95; A61F 2/97; A61F 2002/9528; A61F 2002/9534; A61F 9/007; A61F 9/00736; A61F 2002/9505; A61F 2002/9511; A61F 2002/011
USPC ............................. 606/200, 206; 623/1.11
See application file for complete search history.

(56) References Cited

U.S. PATENT DOCUMENTS

| | | | | |
|---|---|---|---|---|
| 6,296,622 | B1* | 10/2001 | Kurz | A61B 17/12022 604/93.01 |
| 6,478,773 | B1* | 11/2002 | Gandhi | A61B 17/12 604/113 |
| 2002/0161377 | A1* | 10/2002 | Rabkin | A61F 2/95 606/108 |
| 2008/0312681 | A1* | 12/2008 | Ansel | A61B 17/22031 606/200 |
| 2010/0312256 | A1* | 12/2010 | Kassab | A61B 17/0057 606/129 |
| 2012/0109185 | A1* | 5/2012 | Fleenor | A61B 17/2909 606/205 |
| 2014/0180327 | A1* | 6/2014 | Schwab | A61F 5/0036 606/192 |

* cited by examiner

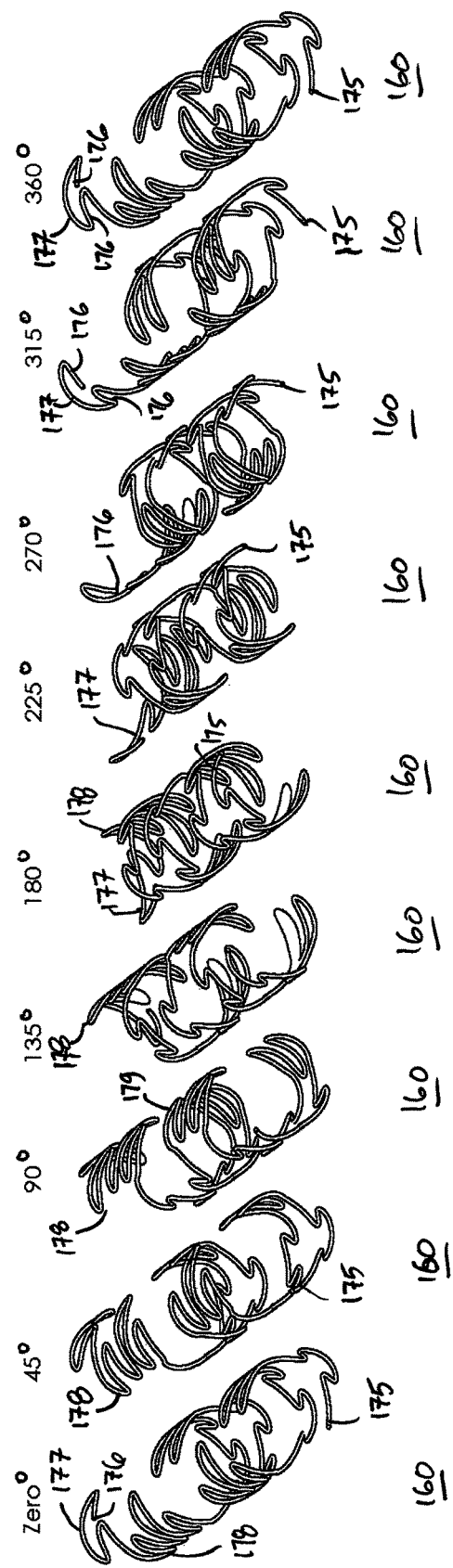

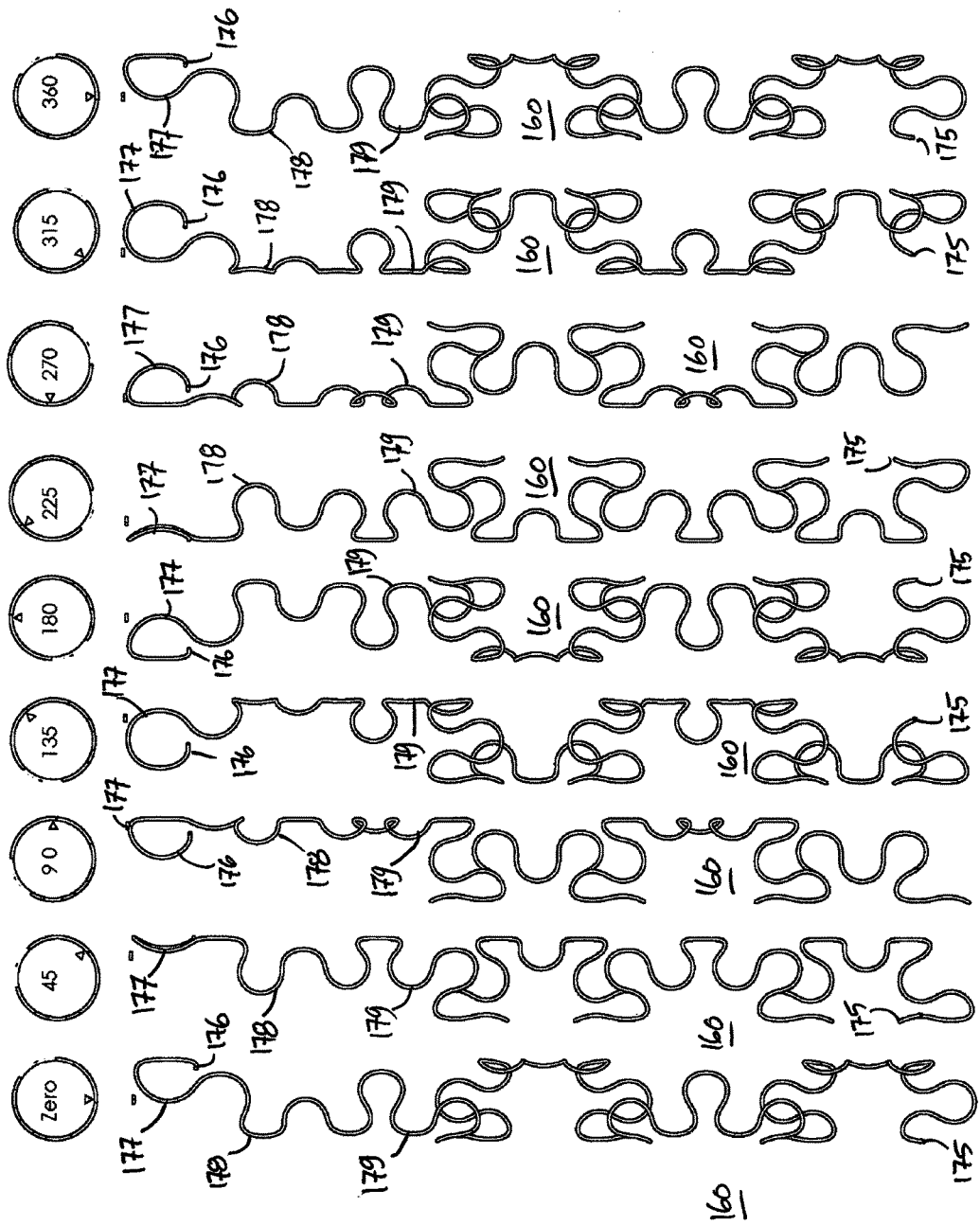

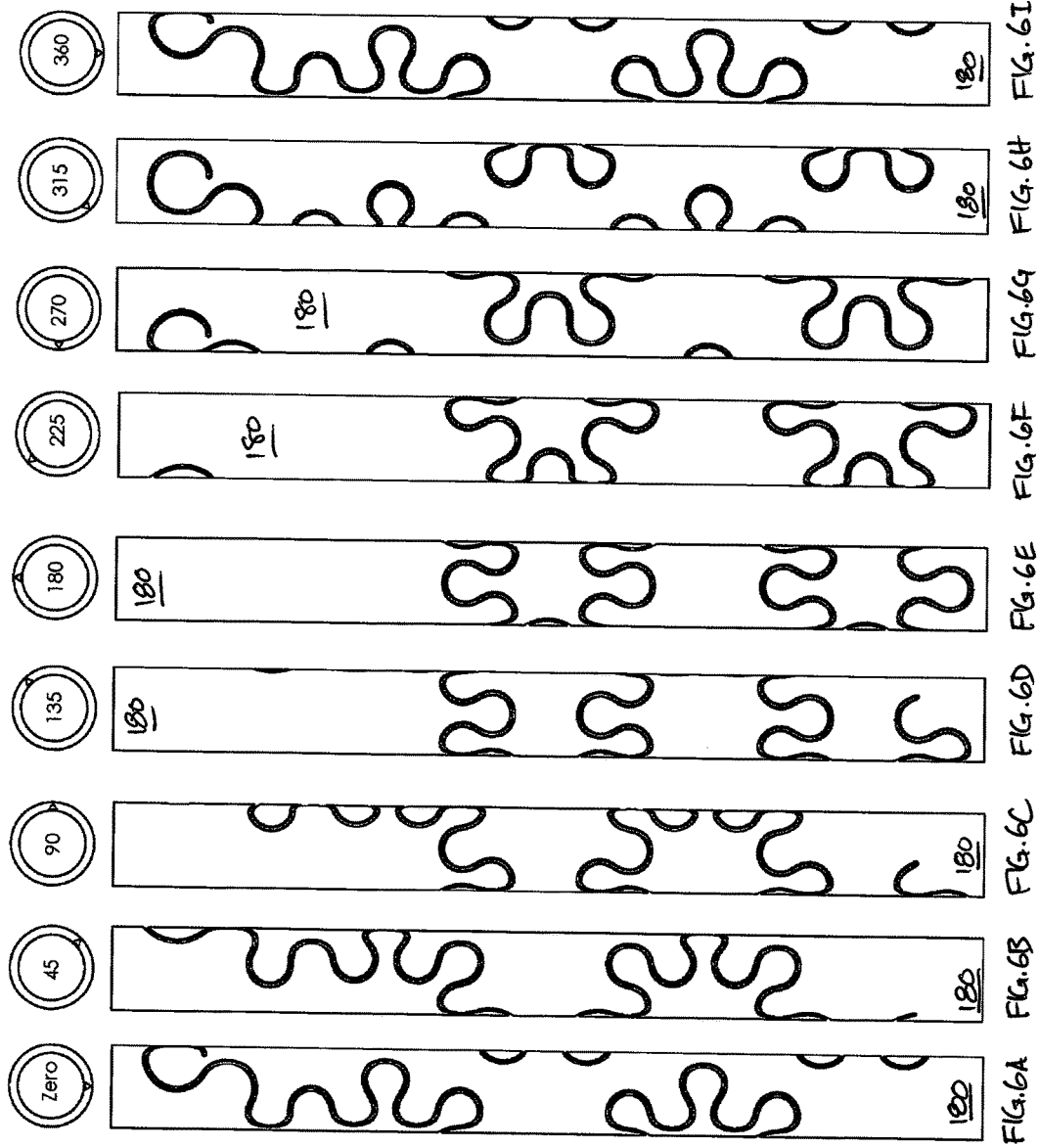

SPRING FOR MOVEABLE JAWS OF DEVICE AND DELIVERY SYSTEM FOR RELEASING THERAPEUTIC APPLIANCE

This application is a continuation-in-part of, and claims priority to, Non-provisional patent application Ser. No. 14/277,022, now pending, filed May 13, 2014 entitled RETRACTABLE AND RAPID DISCONNECT, FLOATING DIAMETER EMBOLIC COIL PRODUCT AND DELIVERY SYSTEM. This application claims priority to Provisional Patent Application No. 62/238,694, filed Oct. 7, 2015 for DEVICE FOR RELEASING THERAPEUTIC APPLIANCE. Each patent application identified above is incorporated here by reference in its entirety to provide continuity of disclosure.

FIELD OF THE INVENTION

The present invention relates to a distal end of a delivery system for deploying an embolic coil and, more particularly, a jaw and spring on the distal end of the delivery system with specific properties so as to be movable between a first position and a second position and returning to the first position that can be used to insert, retract, reconnect, and rapidly disconnect from the embolic coil.

BACKGROUND OF THE INVENTION

Conventional mechanical occlusion devices or coils are used for embolization procedures of AVF, aneurysms, or other vascular lesions. These coils can be deployed accurately to a location, e.g. exactly where the catheter ends. Known catheter systems have no way to retract and/or recapture the coil once deployed. If an end of the coil, or the entire coil, dislodges from the deployed location, there is a significant medical risk that the aneurysm may rip or burst, which can be life threatening. As such, there is a long-felt need in the art to provide an embolic coil and delivery system and method of treatment that can recapture and, therefore, control an embolic coil. There also is a related need to reduce embolization procedure time, cost including the number of embolic coils used, and health risks.

SUMMARY OF THE INVENTION

It is an object of the present invention to provide an assembly, system and method for delivering a vaso-occlusive device or embolic coil with the delivery assembly configured with a gripper assembly with a jaw configured to open and close for delivering the embolic coil to the site of the embolization procedures.

It is an object of the present invention to provide a gripper assembly configured to reconnect the jaw of the gripper assembly to the embolic coil by opening and closing the jaw on the embolic coil, preferably a proximal loop assembly.

It is an object of the present invention to provide a gripper assembly is configured to be actuated to release the embolic coil with no mechanical force being applied by the gripper assembly to disconnect from the embolic coil.

It is an object of the present invention to provide a gripper assembly is configured to deliver the embolic coil to the site, to insert the coil in the aneurysm sac 106, to reconnect to the coil as desired, and to rapidly disconnect from the embolic coil from the delivery system in an embolization procedure.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations, wherein:

FIG. 2 illustrates a perspective view of the spring of a gripper assembly in accordance with an embodiment of the apparatus system, and method of the present invention;

FIGS. 4A through 4I are side and end view of coil illustrating, by rotational degree as indicated, an embodiment of the apparatus system, and method of the present invention;

FIGS. 5A through 5I are side and end view of coil illustrating, by rotational degree as indicated, an embodiment of the apparatus system, and method of the present invention; and FIGS. 6A through 6I are side and end view of a mandrel illustrating, by rotational degree as indicated, an embodiment of the apparatus system, and method of manufacturing the embolic coil product of the present invention.

DESCRIPTION OF THE EMBODIMENTS

Figure 1:
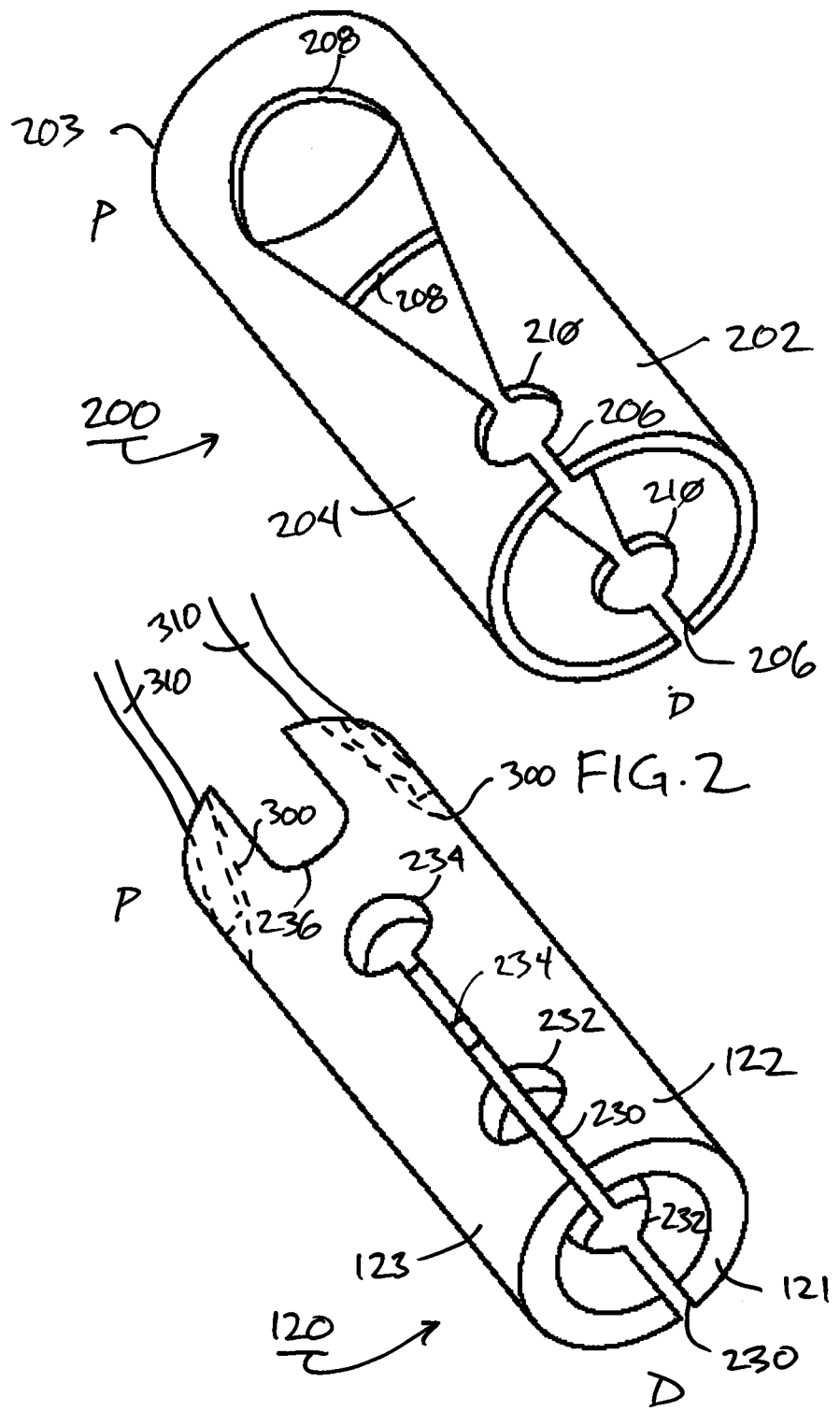
FIG. 1 illustrates a perspective view of the jaw of a gripper assembly in accordance with an embodiment of the apparatus system, and method of the present invention.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "spring" refers to a device of a resilient configuration so as to return to its former shape when released.

As used herein the term "Compartmentalization" refers to when, under certain conditions, the first coil into the aneurysm sac 106 may have "balled" and/or deposited in one corner of the aneurysm sac 106, then such first coil, then, tends to stay in such position resulting in difficulties filling the other parts of the aneurysm sac 106 e.g. using a paintbrush technique to deposit additional coils, and such first coil may block the "neck" e.g. opening between the vessel and the aneurysm sac 106 creating a plug, whereby any of these conditions may cause the aneurysm sac 106 to rupture.

Figure 3:
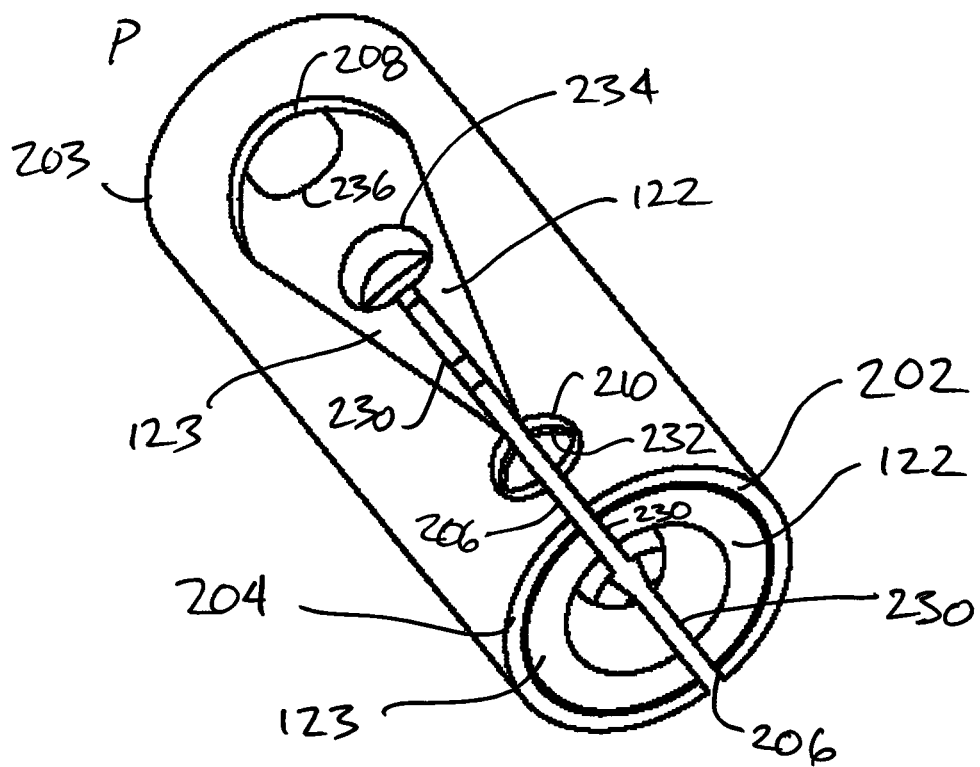
FIG. 3 illustrates a perspective view of the jaw and spring of a gripper assembly in accordance with an embodiment of the apparatus system, and method of the present invention.

As illustrated in FIGS. 1 through 6I, the present invention is described in an embodiment for delivering an embolic coil 160 to the site of an aneurysm sac 106 in a surgical procedure in the body using a gripper assembly 120. As is illustrated in FIG. 1, the gripper assembly 120 configured in a generally cylindrical shape from shape memory alloy, e.g. NitiNOL, that is biased and/or trained to open above body temperature, e.g. 37 degrees Celsius, by applying heat. As shown in FIGS. 2 and 3, a spring 200 also may be formed to receive slidably the gripper assembly 120, the spring 200 configured in a generally cylindrical shape from shape memory alloy, e.g. NitiNOL, that is oppositely biased and/or trained "austenitic" phase thermodynamically stable below body temperature, e.g. 37 degrees Celsius (37° C.). In operation, the jaws 122, 123 of the gripper assembly 120 are opened by supplying electrical current and/or heat to allow the NitiNOL material to change from the Martensitic phase with the jaws 122, 123 in the closed, first position (bent, cooled at around 24 degrees Celsius) to the Austenitic phase having the jaws 122, 123 in the open, second position (intended heat shape-formed). As the spring 200 is in the body, and at the body temperature of 37° C., the NitiNOL material of the jaws 122, 123 to force the jaws 202, 204 open when delivering an embolic coil at the site of the aneurysm sac 106. Upon de-energizing the jaw material 202 the Nitinol returns to about 37° C. and re-enters Martensitic phase allowing the jaws 202, 204 of spring 200 to close jaws 122,123. The embodiment of the present invention is intended to illustrate the operation without limiting the invention as other than NitiNOL material configurations of the spring 200 (e.g. stainless steel, plastic, etc.) in combination with the NitiNOL material operating jaws 122,123 are contemplated and discussed herein.

Referring to FIG. 1, the gripper assembly 120 may be formed with a tip 121 at a distal end D and a generally uniform body portion of a cylindrical shape formed on a proximal end P for attaching to conductive wires 310 using silver epoxy 300. The gripper assembly 120 may be formed with a slot 230 extending a predetermined portion from the tip 121 at the distal end D on either side of the generally cylindrical shape so as to form one or more jaw portions 122, 123 on a distal end D. The slot 230 includes a grip portion 232 for attaching to the wire of an embolic coil. The grip portion 232 may be formed in a generally arcuate shape of a predetermined diameter useful in encompassing the end of an embolic coil such as, for example, the wire diameter, ball, T-end fitting and/or a loop of an embolic coil. The gripper assembly 120 may be configured with a hinge 234 at the end of the slot 230 so as to facilitate opening and closing of the jaw portions 122, 123 utilizing heat supplied by conductive wires 310 according to the desired bias of the shape memory alloy at a range of approximately between 0°-20° degrees Celsius (0-20° C.).

As is illustrated in FIG. 2, the spring 200 may be configured with a proximal end P and a distal end D in a generally uniform body portion of a cylindrical shape dimensioned to receive slidably the gripper assembly 120 at an interior portion thereof such as, for example, a generally cylindrical shape. The spring 200 may be configured with a tip 201 formed in distal end D, a slot 206 extending from the distal end D thereby forming one or more jaws 202, 204. The spring 200 formed with slot 206 and a hinge 208 provides a spring tension from a bias of the one or more jaws 202, 204. The hinge 208 of the spring 200 may be formed in a generally tear-drop shape so as to exert tension on the jaws 122, 123 of the gripper assembly 120. The tear-drop geometry advantageously may be varied in size and dimension to provide a predetermined spring rate or spring tension as well as the radiused tear-drop geometry further resists stresses and cracking over time.

According to an embodiment of the present invention, the spring 200 may be configured in a generally cylindrical shape from a shape memory alloy, e.g. NitiNOL, of a predetermined bias or trained below 37° C. The spring 200 may be configured with an austenitic phase start temperature at or below normal body temperature for example, 37° C. according to an embodiment of the present invention. In another embodiment, the spring 200 may be formed from other materials such as stainless steel, polymers and other than memory shaped alloys (e.g. NitiNOL) whereby a predetermined spring tension may be formed in such other materials so as to accomplish the function of the spring 200 in closing the jaws 122, 123. A proximal end P of the spring 200 may be secured to the gripper assembly 120 by suitable fasteners such as, for example, weld, crimping, press fit, and/or secured by adhesives such as, for example, medical grade polymers, resin, epoxy and the like (e.g. a suitable Polyether Block Amide is manufactured by Foster Corporation of 45 Ridge Rd, Putnam Conn. 06260 under the trademark Pebax®).

Referring to FIG. 2, a spring grip portion 210 may be formed in a generally arcuate shape of a predetermined diameter that may be aligned with the grip portion 232 of the gripper assembly 120. In a similar manner, the spring grip portion 210 is used in encompassing the end of an embolic coil such as, for example, the wire diameter, ball, and/or T-end of an embolic coil. The hinge 208 extends from the grip portion 210 at the end of the slot 206 so as to facilitate opening and closing of the jaw portions 122, 123 utilizing heat supplied by conductive wires 310 according to the desired bias of the shape memory alloy, e.g. NitiNOL.

In operation, the spring 200 may be configured with a bias such that when the hinge 208 of the spring 200 is aligned with the hinge 234 of the gripper assembly 120 the spring acts to close the gripper assembly. According to an embodiment of the present invention, as relating to a delivery system for deploying an embolic coil from the distal and D, the jaws 122, 123 of the gripper assembly 120 and the jaws 202, 204 of the spring 200 are configured to be movable between a first position and a second position with the ability to return and close to the first position. Advantageously, opening and closing of the jaw portions 122, 123 utilizing heat supplied by conductive wires 310 according to the desired bias of the shape memory alloy, e.g. NitiNOL may be used to insert, retract, reconnect, and rapidly disconnect from the embolic coil.

As is illustrated in FIG. 1, directly connecting using silver filled epoxy 300 for actuation by conductive wires 310 to the proximal end P of the gripper assembly 120 allows actuation of one or more jaw(s) 122,123 between an open and closed position by heating the NitiNOL, which may be provided through the connection between materials by supplying electrical current using conductive silver epoxy wires 310 to the proximal end P. The supply of electrical current causes heat and allows the NitiNOL to change from the Martensitic phase (bent, cooled) to the Austenitic phase (intended heat shape-formed) in a known manner Referring to FIG. 1, a connection may be formed between the proximal end P and the conductive wires 310 through the silver filled epoxy 300 on an interior surface of the gripper assembly 120 and a suitable conductive epoxy may obtained from Johnson Matthey J M Part No. 83174. In this manner, the wires 310 may be disposed in the supportive coil of the delivery device utilized to deliver the tip 121 to the site of the surgical procedure. The tip connector 300 may be formed from electrically-, thermally-conductive material (e.g. silver filled epoxy) so as to open and close the jaw(s) 122, 123 by applying and removing heat and/or current. As is illustrated in FIG. 1, the silver filled epoxy connection 300 may be on the interior surface of the proximal end P.

Referring to FIGS. 4A through 6I, the present invention also relates to an embolic coil 160 product and method of manufacturing an embolic coil on a mandrel 180. As shown in FIGS. 4A through 4I and FIGS. 5A through 5I, an embolic coil 160 may be configured with a proximal end 175, a primary coil structure for framing of the aneurysm sac 106 comprised of a distal end or an anchor 176, a primary loop 177, and a secondary coil structure for filling the aneurysm sac 106 comprised of a secondary loop 178 and filler loops 179. The primary and secondary coil structure allows the embolic coil 180 to conform to a diameter and/or the shape of an aneurysm sac 106 as well as to fit a range of aneurysm sac 106 diameter(s). In this manner, the actual shape of coil helps the physician squeeze a third dimension to fit the aneurysm sac 106, which is generally irregular, and as needed for safe and durable treatment.

According to an embodiment of the present invention, as illustrated in As shown in FIGS. 4A through 4I and FIGS. 5A through 5I, the embolic coil 160 has an anchor or a distal G-looped end 176 that may be configured to anchor and/or stop the distal G-looped end 176 such as, for example, when inserting the first coil the distal G-looped end 176 stops and holds so that the remaining part of the coil 160 may be paint-brushed into the aneurysm sac 106 in a surgical procedure. Additionally, the embolic coil 160 may be configured with primary coil 177 for framing of the aneurysm sac 106 such that when the coil exits the distal tip of a delivery system (e.g. micro catheter) inside the aneurysm, the first omega primary loop 177 exits and since it is smaller than the aneurysm sac 106, the primary loop curves inside and anchors the coil using the anchor 176. The remaining length of the embolic coil 160 may be deposited in the aneurism sac 106 similar to a using a paintbrush using the micro catheter tip and to fill the sac 106. The unique preventing it from so called compartmentalization as the first deployed coil and the primary and secondary coils for subsequent filling of the aneurysm sac 106. Moreover, once the distal G-looped end 176 is anchored, the initial secondary coil 178 acts and/or bends with the anchor of the distal G-looped end 176 to creating cantilever with the remaining coil folding to the inner surface of the aneurysm sac 106. According to an advantage of the present invention, the framing of the embolic coil 160 holds the aneurysm sac 106 open by pushing on the interior surface of the aneurysm sac 106 so as to allow ease of further framing with inserting subsequent embolic coils 160 to fill sufficiently the aneurysm sac 106.

The embolic coil 160 for treatment of an aneurysm (herein "vaso-occlusive device") according to the present invention has a specific pattern of primary coils and secondary coils that accomplish the filling of the inner surface of the aneurysm in a more efficient way. The primary coil 177 ("framing") is useful for framing, the structure and scaffolding to engage in a macro sense the inner surface of the wall. The secondary coil 178 ("filler or filling") is used for filling the void spaces of the aneurysm sac 106. When unfolded in the aneurysm sac 106 the embolic coil 160 of the present invention engaging the contours of the inner surface (that may not be spherical), the large loops of the primary coil 177 serve to frame the inner surface;

the smaller loops of the secondary coil 178 unfold in angular patterns jutting out and creating a more efficient fill.

The unique feature of the design is that three dimensional shape of the device is made by two dimensional elements different than current conventional coil designs. For example, conventional three-dimensional coils achieve a three-dimensional shape by straight curves in two dimensions, whereas the present invention provides a three-dimensional shape using an embolic coil 160 design configured with large omega shape curves as well as alternating smaller omega shaped curves that provide the large omegas curves softness as well as improved flexibility. Accordingly, this feature of the present invention enables the construction of the embolic coil 160, as shown in FIGS. 4A-4I and FIGS. 5A-5I, using the mandrel 180, as shown in FIGS. 6A-6I, to have improved adaptation to the shape of the aneurismal sac 106 as well as to fit a range of aneurysm sac 106 diameter(s). The actual shape of embolic coil 160 helps the physician performing the surgical procedure to squeeze the third dimension to fit the aneurysm sac 106 which is generally irregular, as needed for safe and durable treatment.

According to an embodiment of the present invention, the embolic coils 160 are configured to have special properties of a self-adaptive floating diameter that causes the embolic coil 160 to uncoil and frame into the particular shape and diameter of the aneurysm sac 106, which is an improvement over conventional coils as each of the aneurysm sac 106 is a different diameter and/or shape. The special properties are due to a combination of the structure and predetermined shape 167 and other factors. The ability of the embolic coil 160 to self-adapt to the diameter of the aneurism sac 106 allows the first inserted embolic coil 160 to fill and stabilize to the actual wall shape or diameter of the aneurysm sac 106 thereby creating a stabilizing structure or scaffold. Subsequently inserted embolic coil(s) 160 fill the inner volume of the framing structure created by the first inserted embolic coil 160 causing blood to coagulate and form thrombus which fills the aneurysm cavity, thereby preventing the rupture of the aneurysm and the subsequent bleed As is illustrated in FIGS. 4A-4I and 5A-5I, the embolic coil 160 is presented by rotational degrees as shown. Referring to FIGS. 4A-4I, a perspective and end view shows the distal curled end 175 that is finished so as not to create any tissue damage in the patient's body. A distal end 176 is formed in a proximal closed end that also is finished so as not to create any tissue damage in the patient's body. In some versions, an atraumatic tip 171 as described above is secured to the distal end 176. The orthogonally looped proximal end 161, T-bit 172 or curled proximal end 175 is useful for insertion, reconnecting and/or repositioning the embolic coil 160 with the opening 124 and recess 125 combining to grab the proximal end using the jaw(s) 122, 123 of the gripper assembly 120 according to embodiments of the present invention. Accordingly, the orthogonally looped proximal end 161, T-bit 172 or curled proximal end 175 advantageously provides a connection for the jaw 122, 123 movements orthogonal to the plane of the embolic coil 160 primary winding 163 so that the jaw(s) 122, 123 do not exert or impart any force, or an ultra low force, to the embolic coil 160 when disengaging and/or disconnecting the connection to the embolic coil 160. Referring to FIGS. 5A-5I, a side and end view shows the distal curled end 175; however, for sake of clarity, the pattern is selected from one of the predetermined shapes 167 of the set of primary 164, secondary 166, tertiary 168 and/or ordinal 169 arrangements to achieve specific properties conforming to a diameter of an aneurysm thereby taking the shape of the aneurysm using a method and delivery assembly that can be used to insert, retract, reconnect, and rapidly disconnect from the embolic coil, and such end view may not be connected in a 360 degree loop along the length of the embolic coil 160.

Referring to FIGS. 6A through 6H, an embodiment of the present invention further includes a mandrel utilized in the method of manufacturing the embolic coil product. The embolic coil 160 manufactured on the mandrel 180 (FIG. 6A-6I) results in the embolic coil 160 product produced from the method of manufacturing that has the improved properties of a self-adaptive floating diameter that causes the embolic coil 160 to uncoil and frame into the particular shape and diameter of the aneurism sac 106. The embolic coil 160 is represents an ordinal 169 arrangement of the predetermined shape 167 comprising a diameter formed of primary 177 and secondary 178 loops. Accordingly, the embolic coil 160 advantageously is of the predetermined shape 167 of primary loop 177, secondary loop 178 and filler loop 179 between the proximal curled end 175 and distal G-loop end 176. The predetermined shape 167 is selected from the set of primary 164, secondary 166, tertiary 168 and/or ordinal 169 arrangements to create the specific properties conforming to a diameter of any aneurysm sac 106. For example, the embolic coil 160 wants to float to a shape and/or a diameter of an inner surface of the aneurysm sac 106, which permits the self-adaptive floating diameter coil 160 to be used efficiently for a range of aneurysm sac 106(s) that is also not available in the art, e.g. for a diameter range of 4 mm to 6 mm; 5 mm to 7 mm, and 6 mm to 9 mm. The mandrel 180 is shown that is utilized to fabricate a predetermined shape 167 of the embolic coil 160 according to an embodiment of the present invention.

According to specific properties of the embolic coil 160 delivery system and method of the present invention, the void is filled effectively and efficiently requiring less time of the: surgeon, facility used during the embolization procedure, and patient. Thus, an improved time of embolization procedure is realized by the medical therapeutic embolic device, system and method for an embolization procedure 100 that reduces patient risks and overall costs. Moreover, there also is a significant reduction in the number of embolic coils 160 used—whether primary or secondary coils, framing or filling—and with less required materials there is a further reduction in material costs of the embolization procedure. As a result, the device, system and method 100 advantageously to reduce time, costs, and risks to the patient which is an improvement over the prior art.

Conventional mechanical occlusion devices or coils are used for embolization procedures of AVF, aneurysms, or other vascular lesions. Under certain conditions using conventional coils the first coil deposited into the aneurysm sac may exit the "neck" e.g. opening between the vessel and the aneurysm sac into the vessel, an undesirable dangerous condition. Accordingly, the present invention has a curved distal end adapted to anchor to the inner wall and adapted to curl back in and resist exiting aneurism sac through the neck of the vessel. Advantageously, the embolic coil of the present invention may be deployed accurately to a location, e.g. exactly where the micro catheter ends.

Conventional embolic coils also have numerous designs for forming the primary coil structure along a longitudinal axis; however, such coils have disadvantages may have problems adapting to the shape and/or diameter of the aneurysm sac because the unfolded predetermined three dimensional shape does not conform to the specific shape of the aneurysm sac, which is different each time as the aneurysm sac forms in all different shapes. Conventional mechanical occlusion devices or coils are used for embolization procedures of AVF, aneurysms, or other vascular lesions. These coils can be deployed accurately to a location, e.g. exactly where the catheter ends. Known embolic coils have numerous designs for forming the primary coil structure along a longitudinal axis; however, such coils have disadvantages may have problems adapting to the shape and/or diameter of the aneurysm sac because the unfolded predetermined three dimensional shape does not conform to the specific shape of the aneurysm sac, which is different each time as the aneurysm sac forms in all different shapes.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A device for delivering an embolic coil, said device comprising:

a gripper assembly comprising a body portion formed from a shape-memory alloy, said gripper assembly trained in an open position in an austenitic phase of said shape-memory alloy, said body portion configured with a gripper proximal end and a gripper distal end, said gripper proximal end configured in conductive engagement with a plurality of conductive wires by a conductive adhesive, said gripper distal end configured with a slot extending from said gripper distal end to a gripper hinge on each side of said gripper assembly forming one or more jaw portions, said one or more jaw portions configured to move to said open position by applying an electrical current and/or to move to a closed position by removing said electrical current to move said one or more jaw portions to a martensitic phase; and a spring formed from shape-memory alloy in a superelastic austenitic state configured with an austenitic phase start temperature below 37° C., said spring comprising a spring proximal end and a spring distal end in a generally uniform body portion of a cylindrical shape dimensioned to slidably receive said gripper assembly at an interior portion thereof, said spring comprising a slot extending from said spring distal end to a spring hinge on each side of said spring distal end forming one or more spring jaw portions, said one or more spring jaw portions configured to exert spring tension on said one or more jaw portions of said gripper assembly.

2. The device of claim 1, wherein said slot of said spring is configured with a grip portion adjacent said spring distal end configured to receive said embolic coil.

3. The device of claim 1, wherein said slot of said gripper assembly is configured with a grip portion adjacent said gripper distal end configured to receive said embolic coil.

4. A device for delivering an embolic coil, said device comprising:

a gripper assembly comprising:
a body portion formed from shape-memory alloy, said body portion trained to open at a temperature above body temperature to an open position, said body portion having a gripper proximal end and a gripper distal end, said gripper proximal end configured to be in conductive engagement with a tip connector portion of a delivery device with a plurality of conductive wires secured at said tip connector portion by a conductive adhesive, said body portion configured with a slot extending from said gripper distal end to a gripper hinge on each side of said body portion forming one or more jaw portions, said one or more jaw portions configured to move to an open position by applying an electrical current and/or to move to a closed position by removing said electrical current; and a spring configured with a bias in a closed position, said spring being thermodynamically stable below body temperature such that when a temperature of said spring is below body temperature said bias of said spring is sufficient to move said gripper assembly to said closed position, said spring configured to allow movement of said one or more jaw portions between said closed position and said open position, said spring further comprising:
a spring body portion formed with a spring proximal end and a spring distal end, said spring body portion configured to slidably receive said body portion of said gripper assembly, said spring distal end configured with a slot extending to a spring hinge on each side of said spring body portion forming at least one spring jaw portion, said spring proximal end configured to be affixed to said gripper proximal end having said gripper hinge and said spring hinge in aligned relationship, said spring being formed from a shape-memory alloy.

5. The device of claim 4, wherein said proximal end of said spring is affixed to said proximal end of said gripper assembly by a connection selected from a group consisting of press fit, welding, joining with polymers, resins, conductive epoxy, and crimping.

6. The device of claim 4, wherein said slot of said spring is configured with a grip portion adjacent said spring distal end configured to receive said embolic coil.

7. The device of claim 4, wherein said slot of said gripper assembly is configured with a grip portion adjacent said gripper distal end configured to receive said embolic coil.

* * * * *